United States Patent
Ham et al.

(10) Patent No.: US 12,265,076 B2
(45) Date of Patent: *Apr. 1, 2025

(54) COMPLEMENTARY METAL-OXIDE-SEMICONDUCTOR (CMOS) MULTI-WELL APPARATUS FOR ELECTRICAL CELL ASSESSMENT

(71) Applicant: President and Fellows of Harvard College, Cambridge, MA (US)

(72) Inventors: Donhee Ham, Cambridge, MA (US); Wenxuan Wu, Cambridge, MA (US); Jeffrey T. Abbott, Cambridge, MA (US); Henry Julian Hinton, Cambridge, MA (US); Hongkun Park, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/891,964

(22) Filed: Aug. 19, 2022

(65) Prior Publication Data
US 2023/0184739 A1 Jun. 15, 2023

Related U.S. Application Data

(63) Continuation of application No. PCT/US2021/037604, filed on Jun. 16, 2021.
(Continued)

(51) Int. Cl.
*B01L 3/00* (2006.01)
*G01N 33/487* (2006.01)

(52) U.S. Cl.
CPC .... *G01N 33/48728* (2013.01); *B01L 3/50853* (2013.01); *B01L 2300/0636* (2013.01);
(Continued)

(58) Field of Classification Search
CPC ................ B01L 2300/0645; B01L 2300/0636
(Continued)

(56) References Cited

U.S. PATENT DOCUMENTS 5,072,194 A 12/1991 Chevallier
5,233,985 A 8/1993 Hudrlik
(Continued)

FOREIGN PATENT DOCUMENTS

DE 19529371 C2 1/1998
EP 1 271 144 A1 1/2003
(Continued)

OTHER PUBLICATIONS

Invitation to Pay Additional Fees for Application No. PCT/US2016/012685 mailed Feb. 24, 2016.
(Continued)

*Primary Examiner* — Natalia Levkovich
(74) *Attorney, Agent, or Firm* — Wolf, Greenfield & Sacks, P.C.

(57) ABSTRACT

Disclosed herein are semiconductor devices to provide a CMOS-compatible, wafer-scale, multi-well platform that can be used for biomedical or other applications, and methods to operate the same. In some embodiments, circuitry is provided underneath a multiple-well array to electrically interface with electrodes in the wells. To interface with electrodes in a large array, circuitry may be fabricated on a single silicon (Si) wafer having a dimension that is at least the same or larger than that of the multiple-well array. According to one aspect of the present disclosure, standard CMOS fabrication process such as those known to be used in a standard semiconductor foundry may be used without expensive customization for complex fabrication procedures. This may help the production cost to be lowered in some cases.

24 Claims, 12 Drawing Sheets

Related U.S. Application Data

(60) Provisional application No. 63/040,412, filed on Jun. 17, 2020.

(52) U.S. Cl.
CPC .................. *B01L 2300/0645* (2013.01); *B01L 2300/0829* (2013.01)

(58) Field of Classification Search
USPC .......................................... 422/82.01, 82.02
See application file for complete search history.

(56) References Cited

U.S. PATENT DOCUMENTS

| | | | |
|---|---|---|---|
| 5,605,612 | A | 2/1997 | Park et al. |
| 6,032,062 | A | 2/2000 | Nisch |
| 7,332,313 | B2 | 2/2008 | Giaever et al. |
| 8,159,300 | B2 | 4/2012 | Masuda et al. |
| 8,227,223 | B2 | 7/2012 | Giaever et al. |
| 9,121,806 | B1 | 9/2015 | Bhansali et al. |
| 9,360,469 | B1 | 6/2016 | Clements et al. |
| 9,700,221 | B2 | 7/2017 | Rajaraman et al. |
| 9,983,198 | B2 | 5/2018 | Chvatal et al. |
| 11,167,131 | B2 | 11/2021 | Isaacs et al. |
| 11,747,321 | B2 | 9/2023 | Ham et al. |
| 11,768,196 | B2 | 9/2023 | Ham et al. |
| 11,774,396 | B2 | 10/2023 | Park et al. |
| 11,833,346 | B2 | 12/2023 | Park et al. |
| 2002/0010415 | A1 | 1/2002 | Simon et al. |
| 2002/0045318 | A1 | 4/2002 | Chen et al. |
| 2002/0182591 | A1 | 12/2002 | Giaever et al. |
| 2002/0190732 | A1 | 12/2002 | Cheng et al. |
| 2003/0100189 | A1 | 5/2003 | Lee et al. |
| 2004/0100290 | A1 | 5/2004 | Pope et al. |
| 2005/0170510 | A1 | 8/2005 | Huang et al. |
| 2005/0253137 | A1 | 11/2005 | Whang et al. |
| 2005/0282284 | A1 | 12/2005 | Rubinsky et al. |
| 2006/0121446 | A1 | 6/2006 | Abassi et al. |
| 2007/0043301 | A1 | 2/2007 | Martinsen et al. |
| 2007/0072257 | A1 | 3/2007 | Negulescu et al. |
| 2007/0087401 | A1 | 4/2007 | Neilson et al. |
| 2007/0187840 | A1 | 8/2007 | Dell'Acqua-Bellavitis et al. |
| 2007/0264634 | A1 | 11/2007 | Bock et al. |
| 2008/0009434 | A1 | 1/2008 | Reches et al. |
| 2008/0218939 | A1 | 9/2008 | Marcus et al. |
| 2009/0146735 | A1 | 6/2009 | Jeong |
| 2009/0205201 | A1 | 8/2009 | Xu et al. |
| 2009/0227066 | A1 | 9/2009 | Joseph et al. |
| 2009/0255801 | A1 | 10/2009 | Hass |
| 2010/0164110 | A1 | 7/2010 | Jin et al. |
| 2010/0304425 | A1 | 12/2010 | Speller |
| 2011/0210718 | A1 | 9/2011 | Vana et al. |
| 2011/0233512 | A1 | 9/2011 | Yang et al. |
| 2011/0253982 | A1 | 10/2011 | Wang et al. |
| 2012/0094328 | A1 | 4/2012 | Park et al. |
| 2012/0157804 | A1 | 6/2012 | Rogers et al. |
| 2012/0182168 | A1 | 7/2012 | Shibata et al. |
| 2013/0041235 | A1 | 2/2013 | Rogers et al. |
| 2013/0041282 | A1 | 2/2013 | Park et al. |
| 2013/0072775 | A1 | 3/2013 | Rogers et al. |
| 2013/0115705 | A1 | 5/2013 | Patolsky et al. |
| 2013/0123136 | A1 | 5/2013 | Abassi et al. |
| 2013/0260467 | A1 | 10/2013 | Park et al. |
| 2013/0338746 | A1 | 12/2013 | Guvanasen et al. |
| 2013/0341734 | A1* | 12/2013 | Merz .................. H01L 21/82 438/49 |
| 2014/0001041 | A1 | 1/2014 | Rahman et al. |
| 2014/0057283 | A1 | 2/2014 | Wang et al. |
| 2015/0005680 | A1 | 1/2015 | Lipani |
| 2015/0027885 | A1 | 1/2015 | Rajaraman et al. |
| 2015/0148863 | A1 | 5/2015 | Yun et al. |
| 2015/0376811 | A1 | 12/2015 | Joung et al. |
| 2015/0377856 | A1 | 12/2015 | Dunbar et al. |
| 2016/0047770 | A1 | 2/2016 | Tyler et al. |
| 2016/0096173 | A1 | 4/2016 | Teich et al. |
| 2016/0245788 | A1 | 8/2016 | Wang et al. |
| 2016/0245790 | A1 | 8/2016 | Kawai et al. |
| 2016/0278713 | A1 | 9/2016 | Shoaran et al. |
| 2017/0058246 | A1 | 3/2017 | Grier, Jr. et al. |
| 2017/0176414 | A1 | 6/2017 | Abdolahad et al. |
| 2017/0336384 | A1 | 11/2017 | Ino et al. |
| 2018/0163165 | A1 | 6/2018 | Grier, Jr. et al. |
| 2018/0169403 | A1 | 6/2018 | Park et al. |
| 2018/0246079 | A1 | 8/2018 | Wang et al. |
| 2020/0064336 | A1 | 2/2020 | Zafar et al. |
| 2020/0292482 | A1 | 9/2020 | Ham et al. |
| 2021/0187280 | A1 | 6/2021 | Park et al. |
| 2021/0236033 | A1 | 8/2021 | Butera et al. |
| 2021/0371846 | A1 | 12/2021 | Ham et al. |
| 2022/0397512 | A1 | 12/2022 | Ham et al. |
| 2023/0014082 | A1 | 1/2023 | Ham et al. |
| 2024/0210380 | A1 | 6/2024 | Ham et al. |
| 2024/0219370 | A1 | 7/2024 | Ham et al. |
| 2024/0255461 | A1 | 8/2024 | Park et al. |

FOREIGN PATENT DOCUMENTS

| | | |
|---|---|---|
| JP | 2008-269725 A | 11/2008 |
| JP | 2016-529889 A | 9/2016 |
| WO | WO 2009/137440 A1 | 11/2009 |
| WO | WO 2012/050876 | 4/2012 |
| WO | WO 2012/050881 | 4/2012 |
| WO | 2015/012955 A1 | 1/2015 |
| WO | WO 2016/112315 | 7/2016 |
| WO | WO 2019/010343 A1 | 1/2019 |
| WO | WO 2019/089495 A1 | 5/2019 |
| WO | WO 2021/257686 A1 | 12/2021 |
| WO | WO 2021/257701 A1 | 12/2021 |
| WO | WO 2021/257705 A1 | 12/2021 |

OTHER PUBLICATIONS

International Search Report and Written Opinion for Application No. PCT/US2016/012685 mailed May 3, 2016.
International Preliminary Report on Patentability for PCT/US2016/012685 mailed Jul. 20, 2017.
Invitation to Pay Additional Fees for Application No. PCT/US18/58081 mailed Jan. 15, 2019.
International Search Report and Written Opinion for Application No. PCT/US18/58081 mailed Mar. 22, 2019.
International Preliminary Report on Patentability for Application No. PCT/US18/58081 mailed May 14, 2020.
Invitation to Pay Additional Fees for Application No. PCT/US18/40969 mailed Aug. 31, 2018.
International Search Report and Written Opinion for Application No. PCT/US18/40969 mailed Nov. 2, 2018.
International Preliminary Report on Patentability for Application No. PCT/US18/40969 mailed Jan. 16, 2020.
Abbott et al., Multi-parametric functional imaging of cell cultures and tissues with a CMOS microelectrode array. Lab Chip. Mar. 29, 2022;22(7):1286-1296. doi: 10.1039/d1lc00878a.
Crescentini et al., Noise limits of CMOS current interfaces for biosensors: a review. IEEE Trans Biomed Circuits Syst. 2014;8(2):278-292.
Kim et al., An area-efficient low-noise CMOS DNA detection sensor for multichannel nanopore applications. Sensors and Actuators B: Chemical. Jan. 2013;176:1051-1055.
Laborde et al., Real-time imaging of microparticles and living cells with CMOS nanocapacitor arrays. Nat Nanotechnol. Sep. 2015;10(9):791-5. doi: 10.1038/nnano.2015.163. Epub Aug. 3, 2015.
Park et al., 1024-Pixel CMOS Multimodality Joint Cellular Sensor/Stimulator Array for Real-Time Holistic Cellular Characterization and Cell-Based Drug Screening. IEEE Trans Biomed Circuits Syst. Feb. 2018; 12(1): 80-94. Author manuscript provided. 45 pages.
International Search Report and Written Opinion mailed Sep. 29, 2021 for Application No. PCT/US2021/037604.
International Search Report and Written Opinion mailed Sep. 22, 2021 for Application No. PCT/US2021/037626.
International Search Report and Written Opinion mailed Sep. 28, 2021 for Application No. PCT/US2021/037630.

(56) References Cited

OTHER PUBLICATIONS

International Preliminary Report on Patentability for Application No. PCT/US2021/37626 mailed Dec. 29, 2022.
International Preliminary Report on Patentability No. PCT/US2021/037630 mailed Dec. 29, 2022.
Abbott et al., CMOS nanoelectrode array for all-electrical intracellular electrophysiological imaging. Nat Nanotechnol. May 2017;12(5):460-466 and supplemental information. doi: 10.1038/nnano.2017.3. Epub Feb. 13, 2017. 37 pages.
Jorgolli, Integrated Nanoscale Tools for Interrogating Living Cells. May 2015. Doctoral dissertation, Harvard University, Graduate School of Arts & Sciences.
International Preliminary Report on Patentability for Application No. PCT/US2021/037604 mailed Dec. 29, 2022.
Giovangrandi et al., Low-cost microelectrode array with integrated heater for extracellular recording of cardiomyocyte cultures using commercial flexible printed circuit technology. Sensors and Actuators B 113. Jan. 17, 2006;113:545-554. Epub Apr. 22, 2005.
Extended European Search Report mailed May 31, 2024 for Application No. EP 21825407.6 mailed May 31, 2024.
Partial Supplementary European Search Report mailed Jun. 12, 2024 for Application No. EP 21825109.8.
Extended European Search Report mailed Sep. 2, 2024 for Application No. EP 21825109.8 mailed Sep. 2, 2024.
Singapore Search Report and Written Opinion dated Jul. 3, 2024 for Application No. SG 11202261181P.
Abbott et al., A nanoelectrode array for obtaining intracellular recordings from thousands of connected neurons. Nat Biomed Eng. Feb. 2020;4(2):232-241. doi: 10.1038/s41551-019-0455-7. Epub Sep. 23, 2019.
Abbott et al., Optimizing nanoelectrode arrays for scalable intracellular electrophysiology. Accounts of Chem Res. Feb. 13, 2018;51(3):600-608.
Guo et al., Controllable in-situ cell electroporation with cell positioning and impedance monitoring using micro electrode array. Sci Rep. Aug. 10, 2016;6:31392. doi: 10.1038/srep31392.
Lopez et al., A multimodal CMOS MEA for high-throughput intracellular action potential measurements and impedance spectroscopy in drug-screening applications. IEEE Journal of Solid-State Circuits. Nov. 2, 2018;53(11):3076-86.
Park et al., A microsystem for sensing and patterning oxidative microgradients during cell culture. Lab Chip. May 2006;6(5):611-22. doi: 10.1039/b516483d. Epub Mar. 16, 2006.
Rahman et al., CellMap: An automated multielectrode array cell culture analysis system based on electrochemical impedance spectroscopy. <https://digitalcommons.usf.edu/etd/586> Retrieved on May 30, 2024. USF Tampa Graduate Theses and Dissertations. Jun. 28, 2007;1-153.
PCT/US2021/037604, Sep. 29, 2021, International Search Report and Written Opinion.
PCT/US2021/037626, Sep. 22, 2021, International Search Report and Written Opinion.
PCT/US2021/037630, Sep. 28, 2021, International Search Report and Written Opinion.
Extended European Search Report for EP 21825487.8 mailed Jun. 7, 2024.
Japanese Office Action mailed Dec. 10, 2024 for Application No. JP 2022-577744.

* cited by examiner

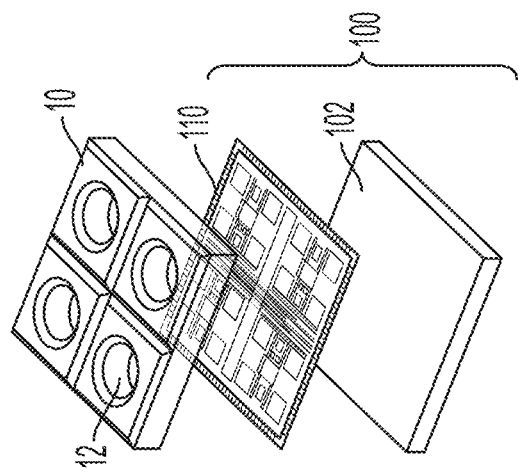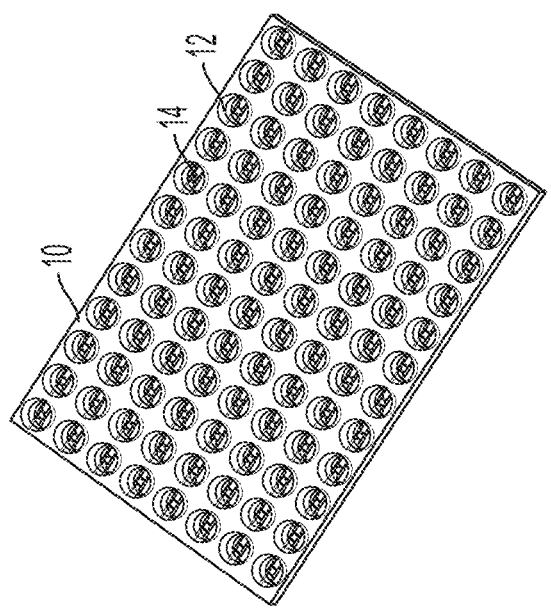
FIG. 2A

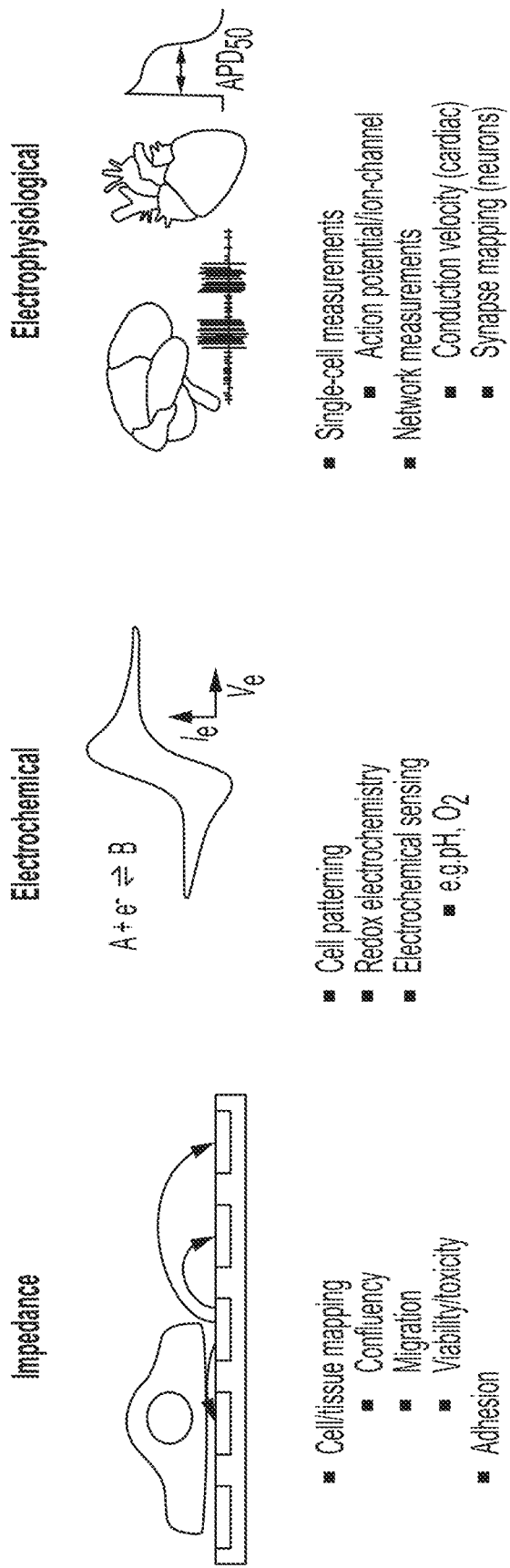

COMPLEMENTARY METAL-OXIDE-SEMICONDUCTOR (CMOS) MULTI-WELL APPARATUS FOR ELECTRICAL CELL ASSESSMENT

CROSS-REFERENCE TO RELATED APPLICATIONS

This application is a continuation of International Application No.: PCT/US2021/037604, filed Jun. 16, 2021, entitled "Complementary Metal-Oxide-Semiconductor (CMOS) Multi-Well Apparatus for Electrical Cell Assessment," which claims the benefit of U.S. Provisional Patent Application Ser. No. 63/040,412, filed Jun. 17, 2020, entitled "Complementary Metal-Oxide-Semiconductor (CMOS) Multi-Well Apparatus for Electrical Cell Assessment," by Ham, et al. each of which is incorporated herein by reference in its entirety.

BACKGROUND

The present disclosure relates to a semiconductor device for electrically assessing cells or other biological specimens in a multiple-well array.

SUMMARY OF THE DISCLOSURE

Disclosed herein are semiconductor devices to provide a CMOS-compatible, wafer-scale, multi-well platform that can be used for biomedical or other applications, and methods to operate the same. In some embodiments, circuitry is provided underneath a multiple-well array to electrically interface with electrodes in the wells. To interface with electrodes in a large array, circuitry may be fabricated on a single silicon (Si) wafer having a dimension that is at least the same or larger than that of the multiple-well array. According to one aspect of the present disclosure, standard CMOS fabrication process such as those known to be used in a standard semiconductor foundry may be used without expensive customization for complex fabrication procedures. This may help the production cost to be lowered in some cases.

Some embodiments relate to a semiconductor device for use with a biochemical or other sensor. The semiconductor device may include a multiple-well array. The semiconductor device may further include a wafer, including at least two reticle areas disposed within the wafer in some instances. Some or all of the reticle areas may have a plurality of circuitry of a same design. Some or all of the reticle areas may include at least one well circuit configured to be in electrical communication with a well of the multiple-well array, a routing circuit configured to route a signal of a first type from a first side of the reticle area towards a second side of the reticle area along a first direction, and to route a signal of a second type from a third side of the reticle area towards a fourth side of the reticle area along a second direction different from the first direction.

In some embodiments, the at least two reticle areas of the semiconductor device may be in electrical communication with each other. The semiconductor device may include a plurality of cross-reticle connections configured to place the at least two reticle areas in electrical communication. The at least two reticle areas may be disposed on a first surface of the wafer. The semiconductor device may include a redistribution layer (RDL) on the first surface, where at least a portion of the plurality of cross-reticle connections may include conductors disposed in the RDL layer. The semiconductor device may include an interposer facing a second surface of the wafer opposite the first surface. The interposer may be a printed circuit board (PCB). The interposer may include a cavity, and the wafer is mounted in the cavity. Some or all of the reticle areas may have a rectangular shape having sides aligned with the first and second directions. The signal of a first type may be a digital signal and the signal of a second type may be an analog signal. A routing circuit in a first reticle area may be configured to receive a signal of the first type from a second reticle area that is adjacent the first reticle area along the first direction. The routing circuit in the first reticle area may be further configured to receive a signal of the second type from a third reticle area that is adjacent the first reticle area along the second direction. The semiconductor device may be configured to be coupled underneath the multiple-well array, such that some or all of the well circuits are in electrical communication with and disposed adjacent a corresponding well in the multiple-well array. The routing circuit may include one or more shift registers configured to route the signal of the first type. The routing circuit may include at least one digital bus, and at least one analog bus. The at least one well circuit may be configured to be in electrical communication with a plurality of electrodes arranged in an electrode array in the well. The plurality of electrodes may include at least 1000 electrodes. The plurality of electrodes may include at least 4000 electrodes. Some or all of the well circuits may include a plurality of peripheral circuits. Some or all of the peripheral circuits may include a stimulation circuit and a recording circuit. The stimulation circuit may include a current injector. The semiconductor device may include one or more switches configured to selectively couple a subset of peripheral circuits within a well circuit to a subset of electrodes within the electrode array. The one or more switches may be further configured to selectively couple a subset of peripheral circuits with one or more optoelectronic components. The one or more optoelectronic components may include a light-emitting diode, a photodetector, or a combination thereof. An electrode of the subset of electrodes may be a reference electrode. The at least two reticle areas may be an array of reticle areas arranged in rows along the first direction and in columns along the second direction, where adjacent reticle areas in some or all of the rows are connected by an array of cross-reticle connections arranged along the second direction, and adjacent reticle areas in some or all of the columns are connected by an array of cross-reticle connections arranged along the first direction. The semiconductor device may be configured to be coupled underneath the multiple-well array, where some or all of the reticle areas are underneath a corresponding well of the multiple-well array. Some or all of the reticle areas may have a width of at least 9 mm. Some or all of the reticle area may have a width of at least 18 mm. Some or all of the reticle areas may include more than one well circuits. The multiple-well array may have at least 96 wells. The wafer may have a lateral dimension that equals or is bigger than a maximum lateral extent of the multiple-well array. The wafer may include silicon. Some or all of the of the reticle areas may be an integrated circuit that may include complementary metal oxide-semiconductor (CMOS) components.

Some embodiments relate to a method of operating a semiconductor device to test a biochemical sensor that includes a multiple-well array. The semiconductor device comprises a wafer, at least two reticle areas disposed within the wafer. Some or all of the reticle areas have a plurality of circuitry of a same design, and some or all of the reticle areas comprises at least one well circuit and a routing circuit. The method of operating may include electrically communicating, using the at least one well circuit, with a well of the multiple-well array; routing, with the routing circuit, a signal of a first type from a first side of the reticle area towards a second side of the reticle area along a first direction, and a signal of a second type from a third side of the reticle area towards a fourth side of the reticle area along a second direction different from the first direction.

In some embodiments, the signal of a first type may be a digital signal and the signal of a second type may be an analog signal. Routing the signal of the first type and the signal of the second type may include: transmitting a signal of the first type from a second reticle area to a first reticle area that is adjacent the second reticle area along the first direction; and transmitting a signal of the second type from a third reticle area to the first reticle area, where the third reticle area is adjacent the first reticle area along the second direction. Electrically communicating with the well may include: providing one or more stimulus to a cell disposed in the multiple-well array, measuring one or more characteristics of the cell, or a combination thereof. The one or more characteristics of the cell may include: an impedance, an adhesion, a redox potential, an action potential, a conduction velocity, a synapse mapping, or a combination thereof. The one or more stimulus may include a current or a voltage. Some or all of the well circuits may include a plurality of peripheral circuits. Some or all of the peripheral circuits may include a stimulation circuit and a recording circuit, and where electrically communicating with the well further may include: selectively coupling, with one or more switches in the semiconductor device, a subset of peripheral circuits within the well circuit to a subset of electrodes within an electrode array in the well; providing, with the stimulation circuits in the subset of peripheral circuits, one or more stimulus to the cell via the subset of electrodes; and measuring, with the recording circuits in the subset of peripheral circuits, one or more characteristics of the cell via the subset of electrodes. The method may include: selectively coupling an optoelectronic component with a peripheral circuit; with the optoelectronic component, emitting a light signal to or receiving a light signal from the cell disposed in the multiple-well array.

Some embodiments relate to an apparatus for electrical assessment of a biological specimen. The apparatus may include a plate having a multiple-well array for holding the biological specimen, each well of the multiple-well array having a plurality of electrodes disposed therein; a wafer having a first surface facing a first side of the plate, may include: an array of reticle areas, each reticle area having a plurality of circuitry of a same design, where each reticle area may include: at least one well circuit configured to be in electrical communication with electrodes in a well of the multiple-well array, a routing circuit configured to route a signal of a first type from a first side of the reticle area towards a second side of the reticle area along a first direction, and to route a signal of a second type from a third side of the reticle area towards a fourth side of the reticle area along a second direction different from the first direction. The apparatus further may include a first substrate having a wafer attach surface facing a second surface of the wafer opposite the first surface, the first substrate may include a plurality of conductors that electrically connect at least a portion of the array of reticle areas to a plurality of pads disposed on a mounting surface of the first substrate opposite the wafer attach surface.

In some embodiments, the first substrate is an interposer that may include a cavity, where the wafer attach surface is disposed within the cavity, and where the second surface of the wafer is attached to the wafer attach surface of the first substrate. The apparatus may include a lid coupled to a second side of the plate opposite the first side. The lid may include a plurality of reference electrodes. Some or all of the reference electrodes may extend into a corresponding well of the multiple-well array. The lid may include a plurality of photoemitters. Some or all of the photoemitters may be facing a corresponding well of the multiple-well array. The apparatus may include a second substrate having a plurality of conductive structures disposed at a first surface facing the mounting surface of the first substrate. Some or all of the conductive structures may be electrically connected to a corresponding pad of the plurality of pads on the mounting surface of the first substrate. The second substrate and the first substrate may be coupled via a magnetic force. The apparatus may include an enclosure that surrounds the wafer and the plate on at least five sides. The biological specimen may include a plurality of single cells. The plurality of electrodes within a well are configured to be in electrical communication with an interior of a single cell disposed in the well. The signal of a first type may be a digital signal and the signal of a second type is an analog signal. A routing circuit in a first reticle area may be configured to receive a signal of the first type from a second reticle area that is adjacent the first reticle area along the first direction, and the routing circuit in the first reticle area may be further configured to receive a signal of the second type from a third reticle area that is adjacent the first reticle area along the second direction. Some or all of the well circuits may include a plurality of peripheral circuits. Some or all of the peripheral circuits may include a stimulation circuit and a recording circuit, and the apparatus further may include one or more switches configured to selectively couple a subset of peripheral circuits within a well circuit to a subset of electrodes within the plurality of electrodes.

BRIEF DESCRIPTION OF THE DRAWINGS

Various aspects and embodiments will be described with reference to the following figures. It should be appreciated that the figures are not necessarily drawn to scale. Items appearing in multiple figures are indicated by the same reference number in all the figures in which they appear. In the drawings:

FIG. 2A is a high level schematic diagram illustrating an exemplary CMOS-Multiwell Platform, in accordance with some embodiments;

FIGS. 11A, 11B and 11C illustrate several exemplary applications of the apparatus as disclosed herein.

DETAILED DESCRIPTION

Figure 1:
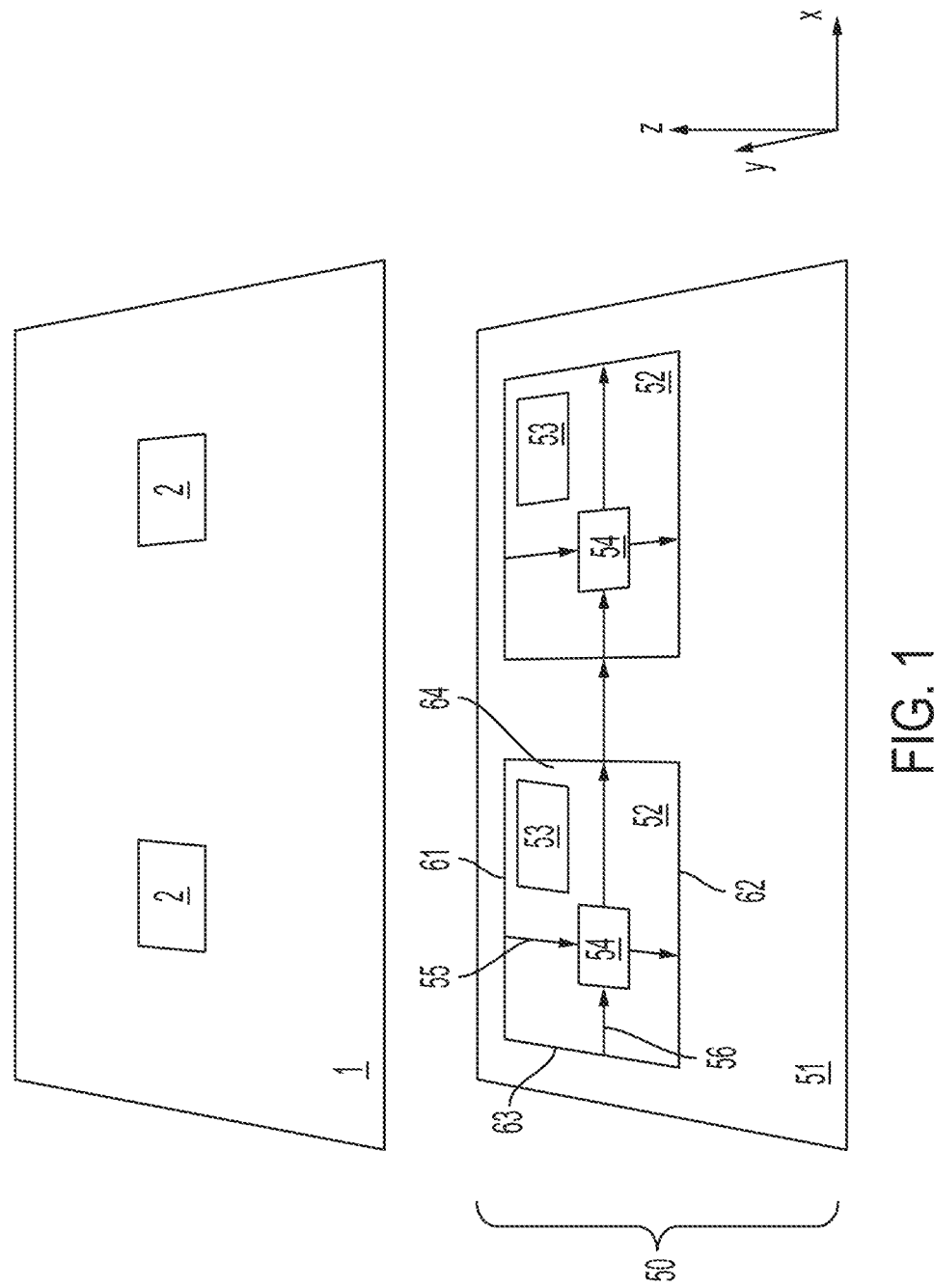
FIG. 1 is a high level block diagram illustrating an exemplary CMOS-Multiwell Platform, in accordance with some embodiments.

The present disclosure is directed to a semiconductor device to provide a CMOS-compatible, wafer-scale, multi-well platform that can be used for biomedical or other applications, and methods to operate the same. In some applications, circuitry is provided underneath a multiple-well array to electrically interface with electrodes in the wells. The platform may sometimes be referred to as a CMOS-Multiwell Platform. The inventors have recognized and appreciated that to interface with electrodes in a large array, circuitry may be fabricated on a single silicon (Si) wafer having a dimension that is at least the same or larger than that of the multiple-well array. According to one aspect of the present disclosure, standard CMOS fabrication processes such as those known to be used in a standard semiconductor foundry may be used, e.g., without expensive customization for complex fabrication procedures, and thus the production cost can be lowered in some cases. The CMOS-Multiwell Platform according to some aspects of this disclosure can be used in applications including electrophysiology studies and general cell assessment using electrical methods, and/or in a high throughput format (e.g. 24-, 96-, and 384-well plate formats).

In some embodiments, the Si wafer is part of a semiconductor device, and has an array of reticle areas, with some or all of the reticle areas having a plurality of circuitry of a same design. The inventors have recognized and appreciated that during manufacturing, reticle areas of a wafer may reuse the same lithographical mask design repeated across the wafer in some cases, thus reducing the cost of tooling and increasing the wafer manufacturing throughput.

According to an aspect, digital and analog circuitry within a reticle area may be arranged to correspond to one or more wells when the multiple-well array is coupled on top of the wafer. Some embodiments can therefore provide a wafer-scale integration of electrical interface with a multiple-well array by using a manufacturing method that does not dice the wafer and/or is compatible with standard using standard CMOS-compatible techniques to reduce manufacturing cost.

Further, according to some aspects, because the reticle areas are spaced apart from each other in accordance with the pitch of the multiple-well array, cross-reticle connections can be provided in the semiconductor device to route power and data signals between reticle areas. The cross-reticle connections may be made using conductors that are disposed in a different plane than the reticle areas, such as in a redistribution layer (RDL) disposed above or below the wafer.

To route the large amount of data signals across the wafer, some or all of the reticle areas of the wafer may comprise well circuits configured to route digital signals along a first direction (X-direction) across a routing area of the reticle area, and to route analog signals along a second direction (Y-direction) across the routing area of the reticle area, e.g., such that digital and analog signals are cascaded from one reticle to the next until an edge of the wafer. Some or all of the reticle areas may also comprise reconfigurable peripheral circuits. Some or all of the peripheral circuits may include a stimulation circuit, a recording circuit, or a combination of one or more of stimulation circuits and recording circuits. The semiconductor device may comprise addressable switches that can selectively couple a subset of peripheral circuits within a well circuit to a selected subset of electrodes disposed within a well above the well circuit. Optionally and in addition to the electrodes, the switches may couple the peripheral circuits to one or more optoelectronic components. Optoelectronic components may be photodetectors or light-emitting diodes, and in some embodiments may be provided in a 1:1 relationship to the number of electrode arrays, such that the functionality for each well above a reticle area can be individually and independently programmed to allow a range of different assessments to be performed within the multiple-well array. The aspects and embodiments describes above, as well as additional aspects and embodiments, are described further below. These aspects and/or embodiments may be used individually, all together, or in any combination of two or more, as the present disclosure is not limited in this respect.

FIG. 1 is a high level block diagram illustrating an exemplary CMOS-Multiwell Platform, in accordance with some embodiments. FIG. 1 shows a semiconductor device 50 that includes a wafer 51. At least two reticle areas 52 are disposed within wafer 51, where some or all the reticle areas have a plurality of circuitry of a same design. Circuitry within each reticle areas 52 includes at least one well circuit 53 and a routing circuit 54. The routing circuit 54 routes a signal of a first type 55 from a first side 61 of the reticle area 52 towards a second side 62 of the reticle area 52 along a first direction y, and routes a signal of a second type 56 from a third side of the reticle area 63 towards a fourth side of the reticle area 64 along a second direction x. Semiconductor device 50 is configured to be used with a biochemical sensor that comprises a multiple-well array. For example, semiconductor device 50 may be coupled to a multiple-well array 1 along the z-direction, such that well circuit 53 in respective reticle area 52 is in electrical communication with a respective well 2 in the multiple-well array 1. The routing circuit 54 may include one or more shift registers 72.

In FIG. 2A, a 96-well plate 10 is provided as part of a biosensor for assessment of biological specimens such as single cells disposed within the arrays of wells 12. The well 12 may have an array of electrodes 14 disposed in the well, for example at a bottom surface of a well 12, to serve as probes that can interface extracellularly or intracellularly with a specimen in the well. The 96-well plate 10 is attached to a semiconductor device 100 that includes a substrate 110 and an interposer 102. In some embodiments, substrate 110 comprises an integrated circuit (IC), and is bonded to an interposer printed circuit board (PCB) via wire-bonding or flip-chip solder bump connection. Circuitry within substrate 110 is situated below each well 12 and are in electrical communication with electrodes 14 disposed in the wells 12.

It should be appreciated that plate 10 is shown as a 96-well array for illustration purposes only, and other aspects of the present disclosure are not so limited, and can be applicable, for example, to 24-well, 384-well, or other suitable multiple-well array formats known in the field.

FIG. 2A is a high level schematic diagram illustrating an exemplary CMOS-Multiwell Platform, in accordance with some embodiments. In FIG. 2A, a 96-well plate 10 is provided as part of a biosensor for assessment of biological specimens such as single cells disposed within the arrays of wells 12. The well 12 may have an array of electrodes 14 disposed in the well, for example at a bottom surface of a well 12, to serve as probes that can interface extracellularly or intracellularly with a specimen in the well. The 96-well plate 10 is attached to a semiconductor device 100 that includes a substrate 110 and an interposer 102. In some embodiments, substrate 110 comprises an integrated circuit (IC), and is bonded to an interposer printed circuit board (PCB) via wire-bonding. Circuitry within substrate 110 is situated below each well 12 and are in electrical communication with electrodes 14 disposed in the wells 12. It should be appreciated that plate 10 is shown as a 96-well array for illustration purposes only, and other aspects of the present disclosure are not so limited, and can be applicable, for example, to 24-well, 384-well, or other suitable multiple-well array formats known in the field.

The number of electrodes in electrode array 14 may be at least 1000, at least 4000, or in some embodiments at least 1 million, as aspects of the present disclosure is not so limited. It should be appreciated that while the electrode array 14 are shown disposed within wells 12 of plate 10, it is not necessary for electrode array 14 to be provided as part of the multiple-well plate, or as a separate component from the semiconductor device 100. In some embodiments, electrode array 14 may be disposed within semiconductor device 100, for example as conductors exposed from an insulative surface of substrate 110 that faces plate 10. In some embodiments, electrode array 14 may be patterned on a surface of substrate 110 as part of the semiconductor fabrication process to form semiconductor device 100, and may be metal pads that comprise Au or Pt, or alloys thereof. In such embodiments, substrate 110 may additionally comprise conductors that interconnect vertically the exposed electrode array 14 to circuitry within substrate 110.

Figures 2B, 2C:
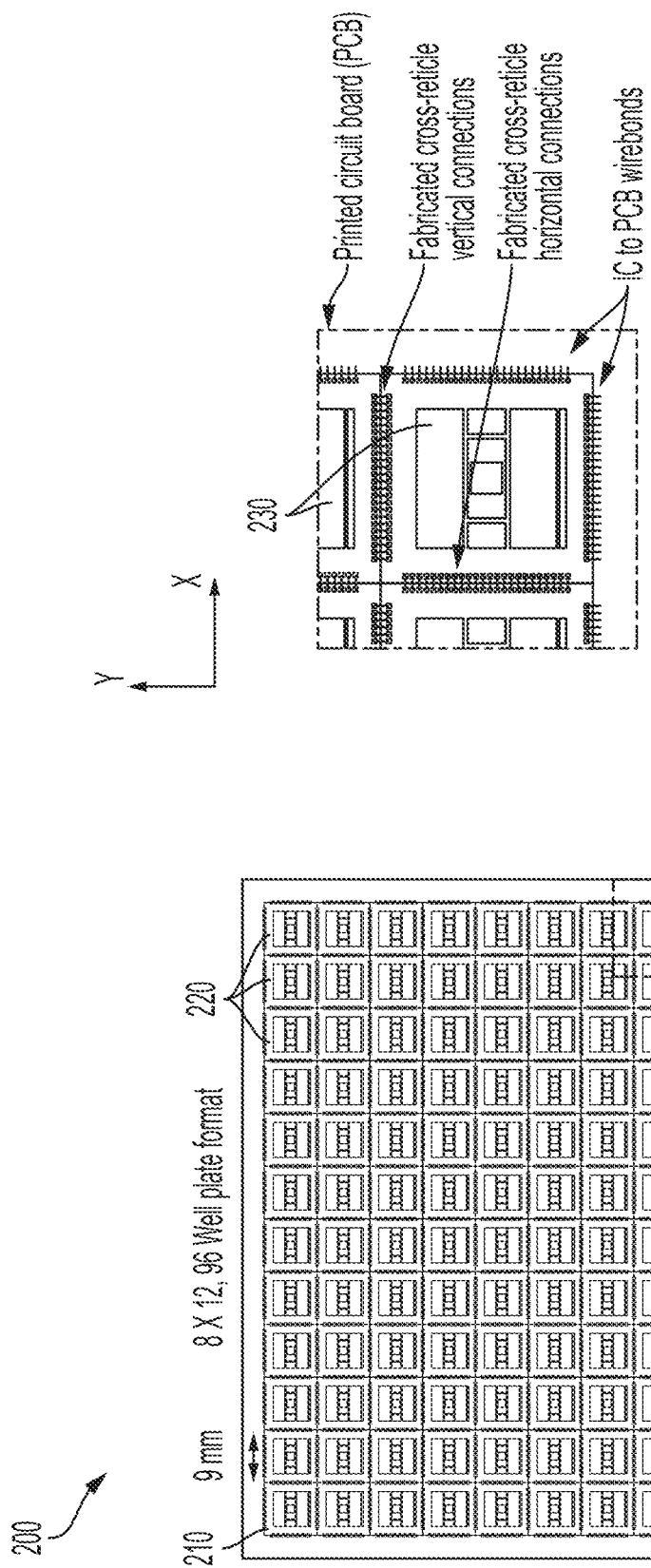
FIG. 2B is a top view schematic diagram of an exemplary semiconductor device that can be used in a CMOS-Multiwell Platform, in accordance with some embodiments.
FIG. 2C is an magnified view of a portion of FIG. 2B.

FIG. 2B is a top view schematic diagram of an exemplary semiconductor device 200 that can be used in a CMOS-Multiwell Platform, in accordance with some embodiments. In FIG. 2B, there are 8×12=96 reticle areas 220 in the substrate 210, and the substrate 210 may be referred to as a multiwell IC. Substrate 210 may be a Si wafer, and each reticle area may be of an identical design that is fabricated by stepping the reticle of a standard lithography process along the X- and Y-directions without the need to dice the wafer. Each reticle area may comprise multiple layers, including an active layer that comprises silicon components, as well as one or more layers comprising conductors and dielectric materials as connections and interconnections. Each reticle area may contain one or more identical well circuits 230, as shown in the magnified view image in FIG. 2C.

In the embodiment shown in FIG. 2B, each reticle area 220 may be a CMOS chip and all 96 chips are connected through cross-reticle connections that can be fabricated using standard semiconductor processing techniques.

Figure 3:
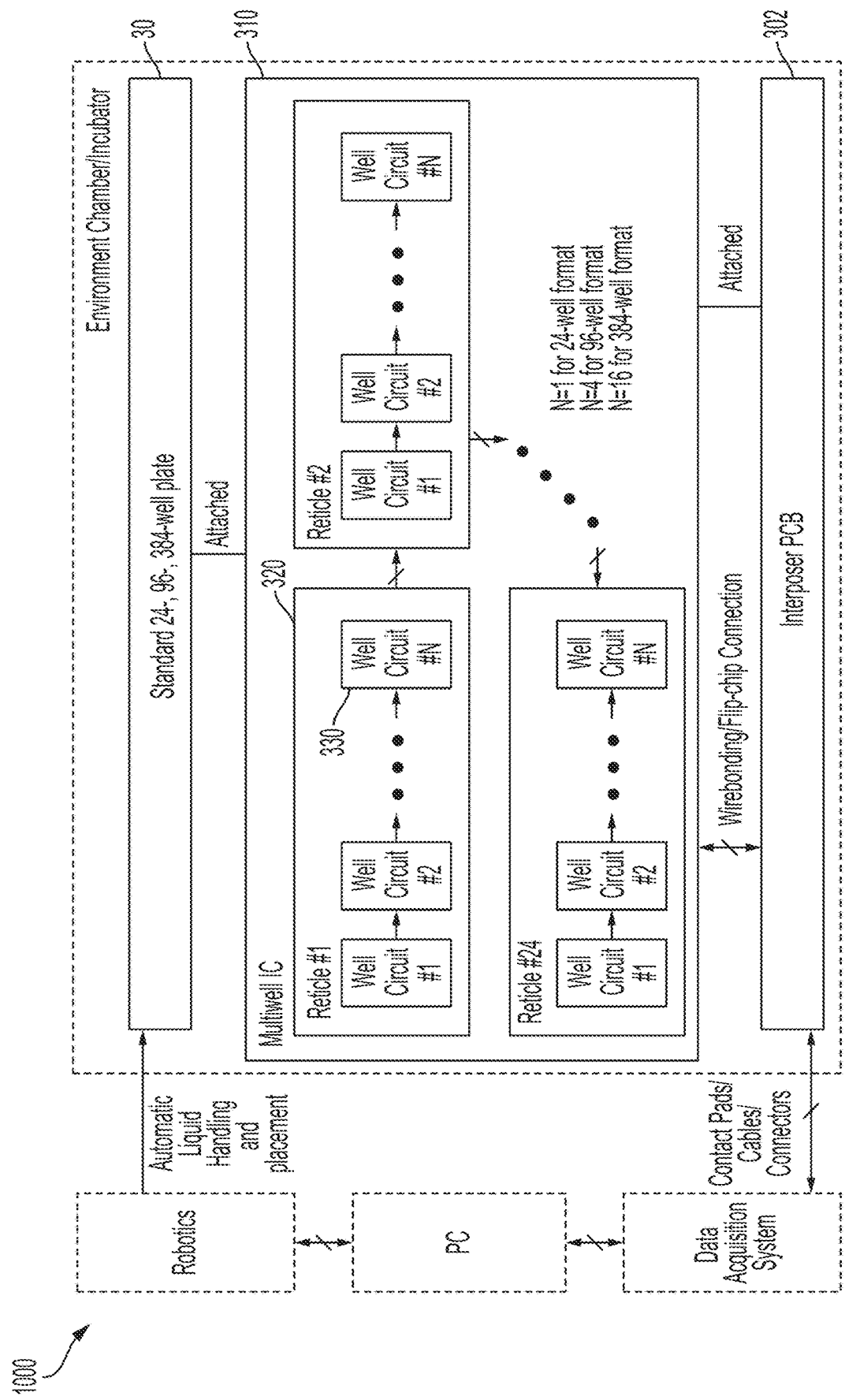
FIG. 3 is a schematic block diagram illustrating an exemplary apparatus for electrical assessment of a biological specimen, in accordance with some embodiments.

FIG. 3 is a schematic block diagram illustrating an exemplary apparatus 1000 for electrical assessment of a biological specimen, in accordance with some embodiments. The apparatus 1000 may be an example of a CMOS-Multiwell Platform, and includes a plate 30 having a multiple-well array. The plate 30 may be a standard 24-, 96- or 384-well plate in some non-limiting examples. The plate 30 is attached mechanically to a wafer 310, which may be a multiwell IC. Wafer 310 may be a silicon wafer that comprise a plurality of reticle areas 320. Reticle areas 320 may be arranged in an array on a surface of wafer 310, and may be un-diced silicon dies. Adjacent reticle areas are in electrical communications with each other, for example via cross-reticle connections. Each reticle area may have an identical circuit design. In some embodiments, each reticle area may have N identical well circuits 330. In the example shown in FIG. 2B, one well circuit is provided to electrically interface with electrodes in one well of the plate 30. For example, when there are 24 reticle areas, N may be 1 for 24-well format, 4 for 96-well format and 16 for 384-well format. However, it should be appreciated that the design of the reticles and well circuits is not limited to providing a one-to-one correspondence with the wells, and more or less than one well circuit may be provided to a well. In some embodiments, the well circuits may be reconfigured, for example by using a plurality of switches, to couple to different wells.

Still referring to FIG. 3, wafer 310 is attached to an interposer 302 both mechanically, and electrically. Any suitable bonding method known in the field of semiconductor packaging may be used to couple wafer 310 with interposer 302, such as but not limited to flip-chip bonding or wire-bonding. Apparatus 1000 may additionally and optionally include components for carrying out electrical assessment of a biological specimen disposed in the wells of plate 30. Such components may include a data acquisition system in communication with contact pads on interposer 302, one or more computers having processors that can execute programs stored in one or more storage medium to implement a method of carrying out testing using the wafer 310. Furthermore, in some embodiments, robotics may be used in connection with plate 30 to provide automatic sample handling and placement.

Figure 4:
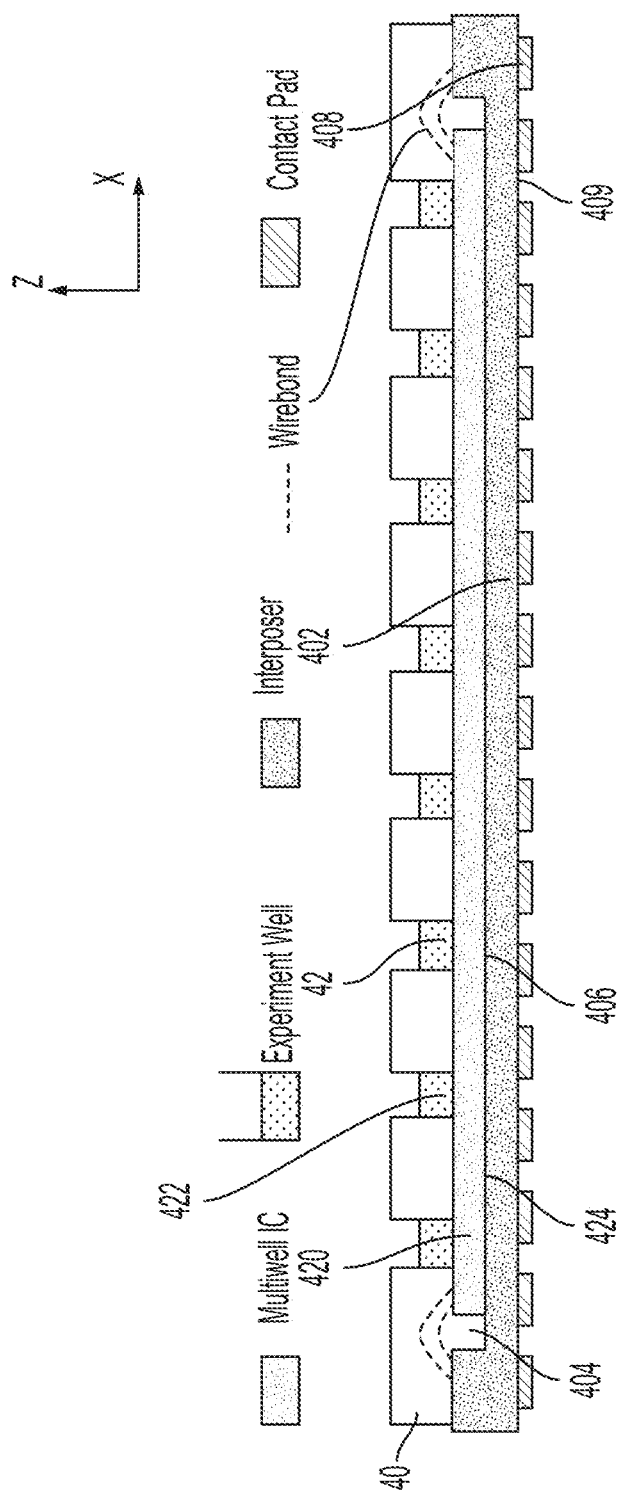
FIG. 4 is a cross-section view schematic diagram of an exemplary apparatus, in accordance with some embodiments.

FIG. 4 is a cross-section view schematic diagram of an exemplary apparatus, in accordance with some embodiments. In FIG. 4, a first surface or top surface 422 of the multiwell IC 420 is facing the wells 42 in the plate 30, while a second or bottom surface 424 of the multiwell IC is facing opposite the wells, and faces the interposer. A plurality of reticle areas (not shown) are disposed in the top surface of the multiwell IC. Multiwell IC 420 is coupled to interposer 402 at a wafer attach surface 406. The interposer 402 may comprise a cavity 404 as shown in FIG. 4, which in some examples may have a cavity height that is similar to the thickness of the wafer that forms multiwell IC 420. Wafer attach surface 406 may be disposed at the bottom surface of cavity 404, and the multiwell IC 420 is positioned inside the cavity 404 and wire-bonded to the interposer 402. The input/output (I/O) of the multiwell IC 420 may be wire-bonded and routed to the contact pads 408 disposed on a mounting surface 409 at the bottom of the interposer 402. It should be appreciated that connection between the interposer and multiwell IC is not limited to wire-bonding as shown in the example in FIG. 4, and in some embodiments may be done via flip-chip bonding, or other techniques. Pads 408 may alternatively be implemented as gold fingers, cables, or connectors (e.g. USB) instead of contact pads. For example, a PCB with center opening and having pads aligned with the pads of a multiwell IC can be used for flip-chip bonding, where a solder bump will connect the interposer pads with the array of pads in the multiwell IC directly without wire-bonding.

As shown in FIG. 4, wells 42 are open bottom wells that are attached onto the multiwell IC 420 and the interposer 402, such that the interior of wells 42 may be fluidically connected to the top surface 422 of multiwell IC 420, although aspects of the present disclosure are not limited to open bottom wells.

Figure 5:
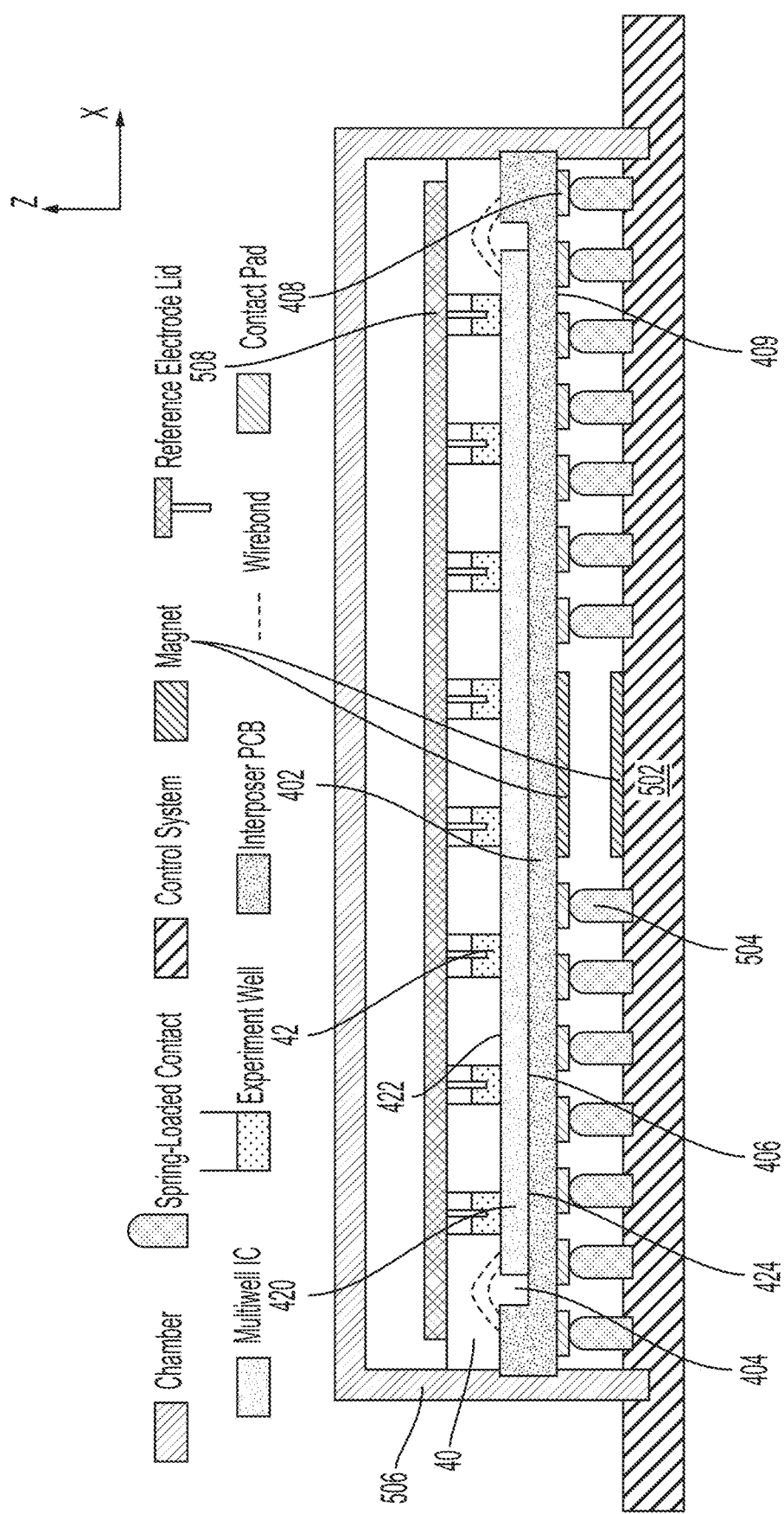
FIG. 5 is a cross-section view schematic diagram of an exemplary apparatus that could interface with an external data acquisition system, in accordance with some embodiments.

FIG. 5 is a cross-section view schematic diagram of an exemplary apparatus that could interface with an external data acquisition system, in accordance with some embodiments. In FIG. 5, components that are similar to those of FIG. 4 are denoted with the same reference numbers. In FIG. 5, an environment chamber or incubator 506 with key slot feature is used to guide the well-plate 40 to align with an array of spring-loaded contacts 504 on a second substrate 502 with matching pattern to the contact pads 408 on the interposer 402. The enclosed chamber 506 provides an isolated environment for the experiment wells 42 with gas control. In some embodiments, second substrate 502 may provide mechanical support and environmental sealing for chamber 506. Furthermore, second substrate 502 may provide electrical interconnections between the multiwell IC 420 within chamber 506 to an external data acquisition system outside of chamber 506. Second substrate 502 may be physically secured to interposer 402 by a suitable clamping technique. In some embodiments, second substrate 502 is coupled to interposer 402 via a magnetic force, for example using a pair of magnets disposed on the mounting surface 409 of interposer 402 and a top surface of second substrate 502, which provides a pulling/snapping force to ensure sufficient contact between the pads 408 and spring-loaded contacts 504.

Figure 6:
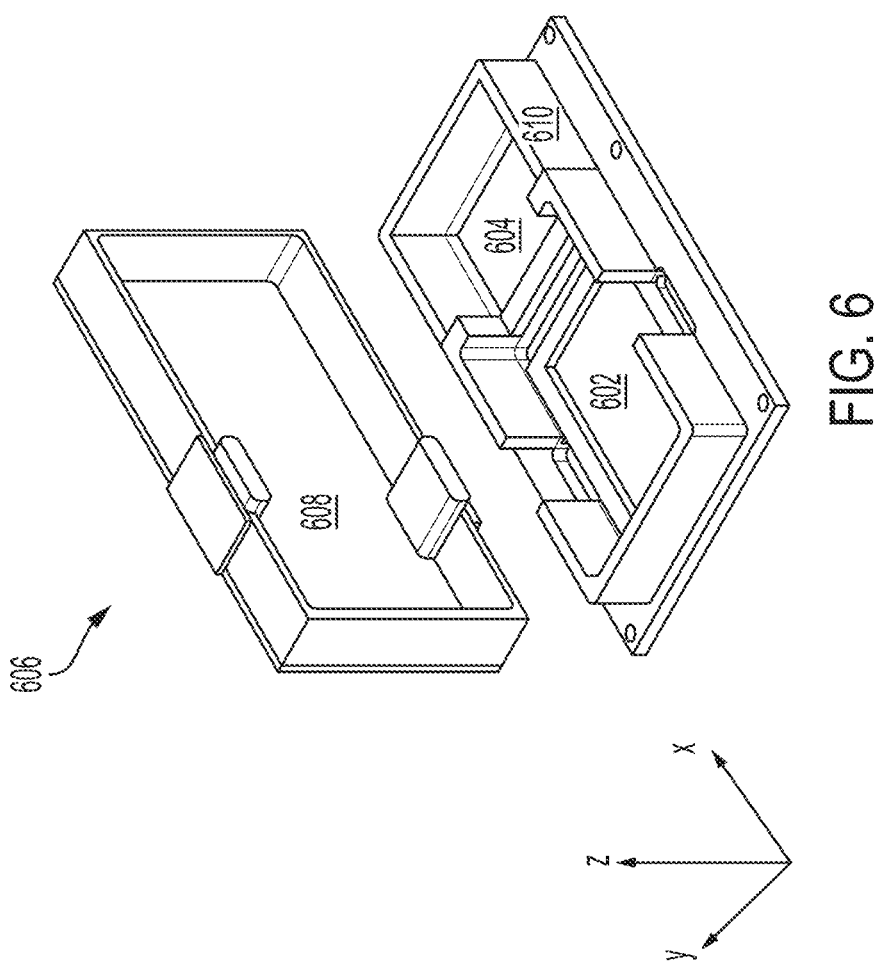
FIG. 6 is a plan-view schematic diagram of an exemplary environment chamber, in accordance with some embodiments.

FIG. 6 is a plan-view schematic diagram of an exemplary environment chamber 606, in accordance with some embodiments. FIG. 6, shows that environment chamber 606 comprises a lid 608 that can snap on to a housing 610 to create an enclosure that has two openings towards the bottom, with opening 602 open to a well-plate, and opening 604 for providing gas control to the environment chamber 606.

Figure 7:
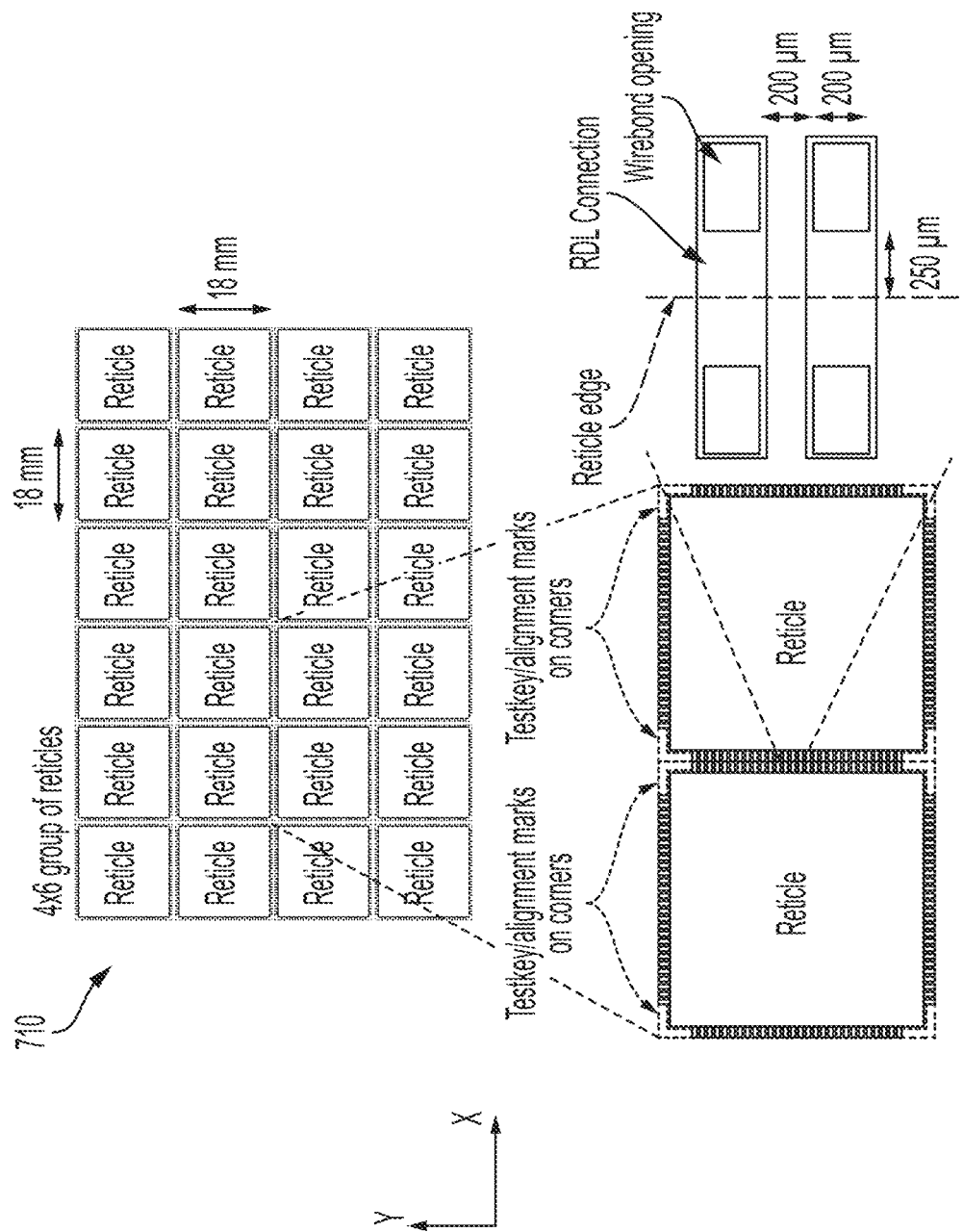
FIG. 7 is a top view schematic diagram illustrating an exemplary wafer, in accordance with some embodiments.

FIG. 7 is a top view schematic diagram illustrating an exemplary wafer 710, in accordance with some embodiments. The wafer 710 may be a multiwell IC and in the example shown consists of 4×6=24 identical reticle areas (e.g. 18 mm×18 mm). The reticle area may be designed in a specific symmetry so that a simple redistribution layer (RDL) connections between the IO pads of neighbor reticle areas will allow I/O signals to pass through the entire wafer. The RDL may comprise conductors such as metal traces that serve as cross-reticle connections interconnect adjacent reticle areas, IO pads disposed around the periphery of wafer 710 may be then wire-bonded to the interposer as shown in FIG. 4.

Figure 8:
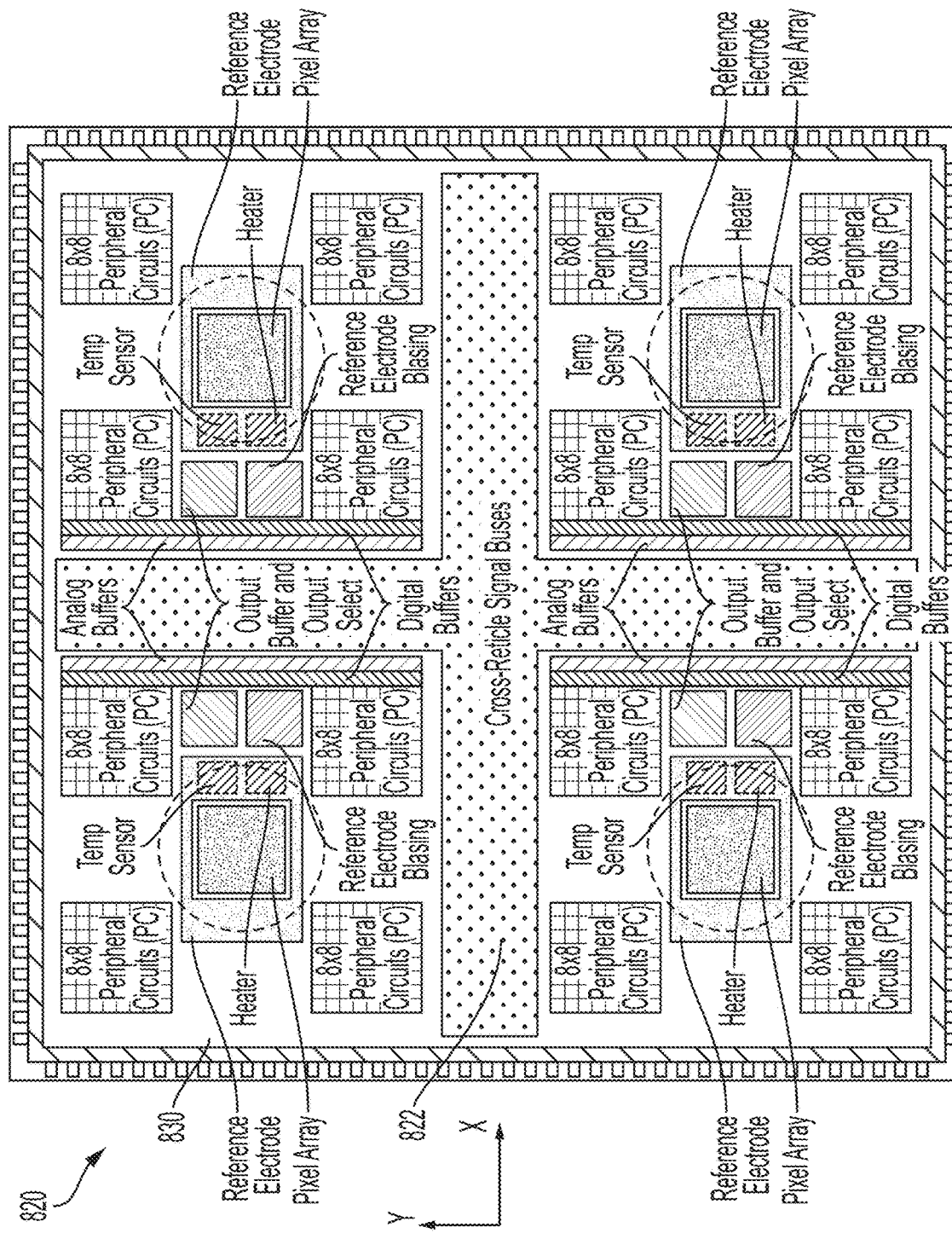
FIG. 8 is a top view schematic diagram illustrating an example circuit design within a reticle area, in accordance with some embodiments.

FIG. 8 is a top view schematic diagram illustrating an example circuit design within a reticle area, in accordance with some embodiments. In FIG. 8, a reticle area contains 4 identical well circuits 830 positioned to allow standard well-plate alignment (e.g. 9 mm distance), although it should be appreciated that variations of the design as shown in FIG. 8 having any suitable number of well circuits may be used for other multiple-well arrays such as 24-well and 384-well plates. For the 24-well version reticle, only one well circuit should be centered at the reticle in this example. For example in a 384-well version reticle area, 16 well circuits may be positioned to allow standard 4.5 mm well distance.

In FIG. 8, reticle area 820 is designed to have left-right and top-bottom symmetric IO pads on the periphery so that signal can be routed cross the reticle area and pass into adjacent reticle areas through the cross-reticle signal buses 820. Each well circuit 830 inside the reticle area 820 may have dedicated signal buffers to buffer the global signal to local well circuit and vice versa. In one embodiment, different types of signals are routed along the X- and Y-directions, to increase routing efficiency when daisy-chaining a plurality of rows and columns of reticle areas. For example, the cross-reticle signal busses 822 may be a routing circuit that routes digital signal along the X-direction from the left side of the reticle area towards the right side, and routes analog signals along the Y-direction from the top side of the reticle area towards the bottom side.

Figure 9:
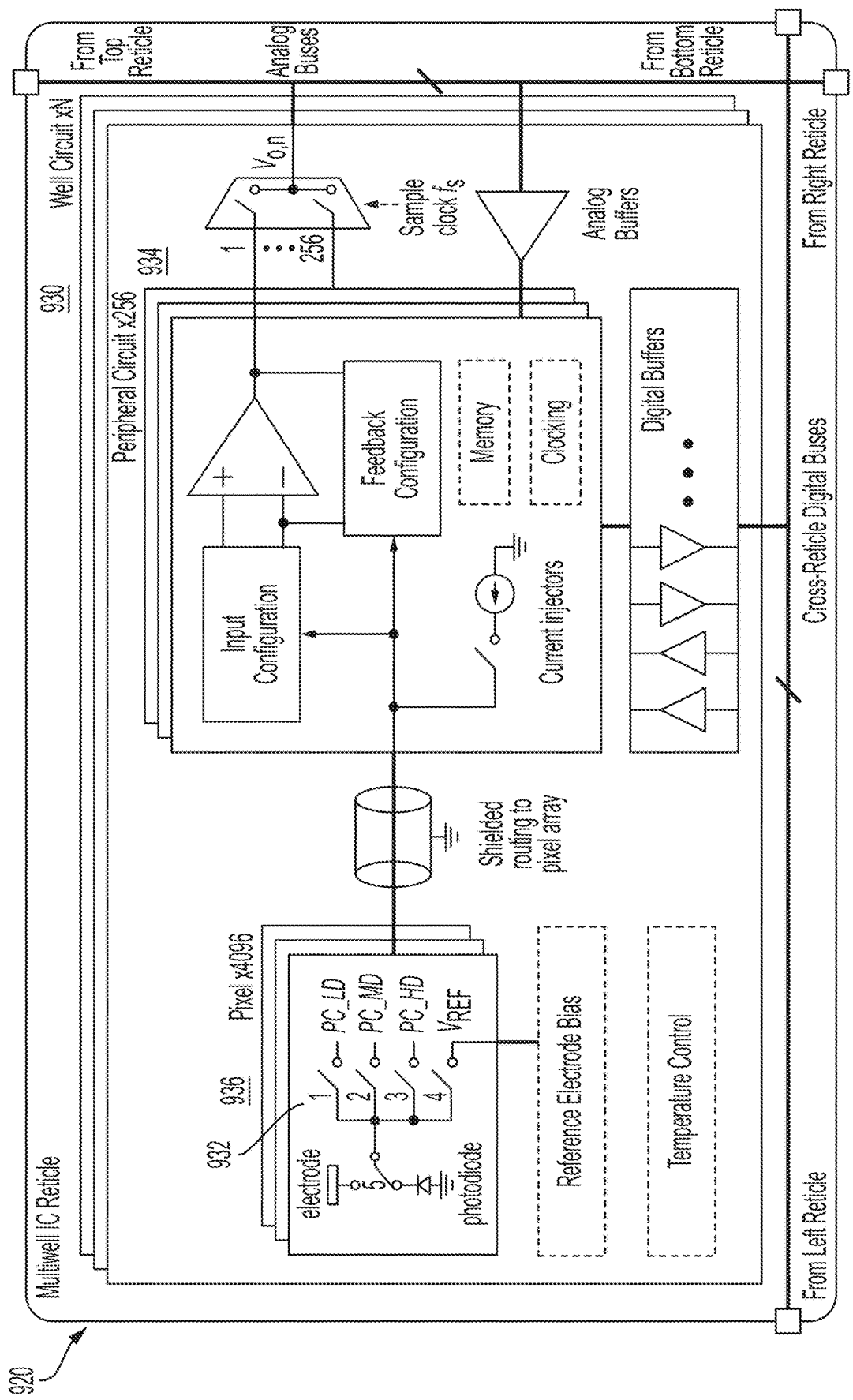
FIG. 9 is a schematic block diagram illustrating an exemplary well circuit inside a reticle area 920, in accordance with some embodiments.

FIG. 9 is a schematic block diagram illustrating an exemplary well circuit 930 inside a reticle area 920, in accordance with some embodiments. In a well circuit 930, a plurality of peripheral circuits 934 are designed to be able to connect to all or a subset of an array of electrodes 936 within a well of a multiple-well array attached atop the wafer that the reticle area 920 is disposed in. The array of electrodes may also be referred to as pixels, each pixel occupying a pixel area. In a non-limiting example, well circuit 930 has 256 peripheral circuits. By selective operation of a plurality of switches 932, all or a subset of the peripheral circuits are able to connect to all or a subset of 4096 pixels in a well to allow high density (HD), medium density (MD) or low density (LD) connections. Any set of arbitrary pixels can also act as reference electrode by connection the electrode to the reference electrode bias ($V_{REF}$) In the non-limiting example described, in HD (MD) connections, a subset of 16×16 (32×32) pixels are recorded out of the total 64×64 available pixels. This routing design allows scanning of the recording area (16×16 for HD and 32×32 for MD) across the entire available active area (64×64). This example design allows customized experiment setups from well to well.

In some embodiments, switches 932 may also selectively couple the peripheral circuits 934 to one or more optoelectronic components instead of an electrode. Examples for the optoelectronic component include photodetectors or photoemitters such as light-emitting diodes, such that the functionality for each well above a reticle area can be individually and independently programmed to allow a range of different assessments to be performed within the multiple-well array. In some embodiments, the optoelectronic component may be a photodiode fabricated on the wafer such as wafer 710, and disposed in an optoelectronic sensing region within a pixel area. In a non-limiting example, a lateral spatial span of the optoelectronic sensing region covers the same area as the electrode array in the pixel area, although it should be appreciated that other suitable placement or dimension for the optoelectronic component may be used. In some embodiments, the optoelectronic interface has a 1:1 mapping with the electrical interface, and an optoelectronic component is provided for each electrode array or each pixel area, although the 1:1 mapping is not a requirement.

Referring back to FIG. 9, the peripheral circuit 934 may each include a stimulation circuit and a recording circuit. In some embodiments, the stimulation circuit may comprise one or more current injectors. Some aspects of the peripheral circuit design are related to current-based stimulators for electrogenic cells and related methods, as disclosed in International Application Publication. No. WO 2019/010343, the disclosure of which is hereby incorporated by reference in its entirety. Some aspects may also be related to electronic circuits for analyzing electrogenic cells and related methods, as disclosed in International Application Publication. No. WO 2019/089495, the disclosure of which is hereby incorporated by reference in its entirety.

Still referring to the design of well circuits in FIG. 9, global digital control and configuration signals may be routed from left to right in the center of the reticle, whereas global analog signals (output and control signals) are routed from top to bottom, also in the center of the reticle as shown in see FIG. 8. In some embodiments, each well circuit buffers in and out its local signals to the global buses.

Digital Interface

According to an aspect of the present disclosure, to allow for simple and fast programming of a multiwell IC such as the wafer 710 as shown in FIG. 7 cross all 24 reticles, three level of Serial-Peripheral-Interface (SPI) may be provided. The highest-level SPI select one or more specific well(s) from the multiwell IC to be programed in the lower level two SPIs. The input ($D_{IN}$) of this SPI may come from an I/O pad on the left side of a reticle area, and the output ($D_{OUT}$) of this SPI is routed to the symmetric I/O pad on the right side of the reticle area, which allows simple RDL connections to daisy-chain the reticles together. The lower two level SPIs may have shared control signals across the entire multiwell IC. In some embodiments, the Address Select SPI select the components (e.g. peripheral circuits and temperature control) within the well circuit to be programed by the Configuration SPI, which write the registers of the selected components in the selected wells.

Analog Output

Further according to an embodiment of the present disclosure, each reticle area may have, for example, 8 analog output buses routed from top I/O pads to bottom I/O pads. The analog output of the peripheral circuits in each well is multiplexed into one of the eight buses. Since each reticle has 4 wells but 8 analog buses, this design allows the top two rows (2×6) of reticle areas to be read out from the top side and the bottom two rows (also 2×6) to be read out from the bottom side of the reticle area, although aspects of the present disclosure are not so limited and other suitable readout schemes may be used. The inventors have recognized and appreciated that the routing of analog and digital signals as described herein may advantageously improve signal routing efficiency by simplifying the routing design. It should be understood, however, that other numbers of analog buses are also possible in other embodiments. Optionally or alternatively, signals can be routed all digitally, after analog signals are converted in analog-to-digital converters within the reticle, and converted back to analog form using digital-to-analog converters when needed to provide stimulation.

Figure 10A:
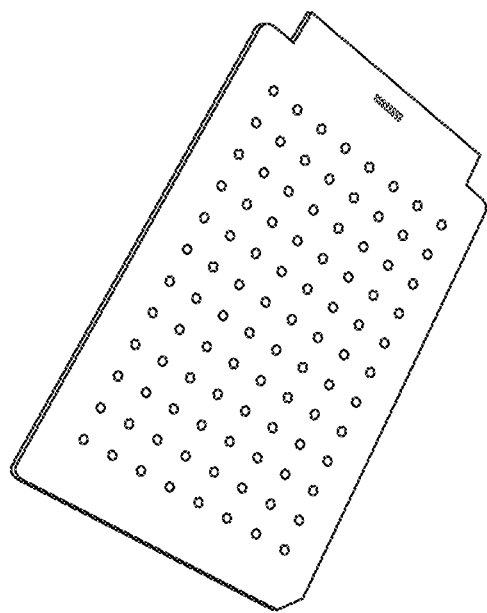
FIGS. 10A and 10B are top view and bottom view schematic diagrams, respectively, of an example design of an environment chamber lid with reference electrodes, in accordance with some embodiments.
Figure 10B:
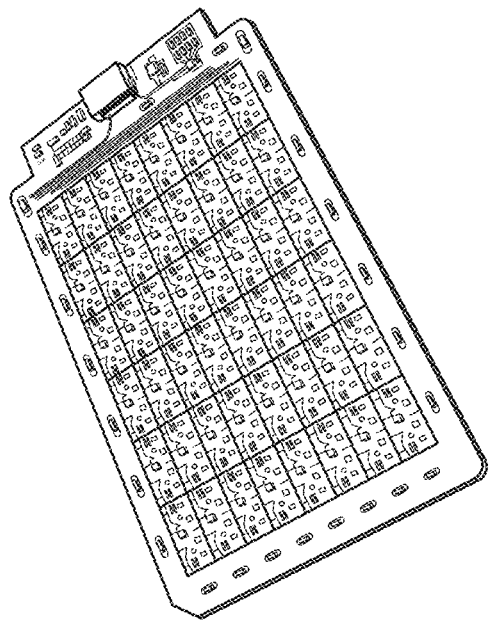

FIGS. 10A and 10B are top view and bottom view schematic diagrams, respectively, of an example design of an environment chamber lid with reference electrodes, in accordance with some embodiments. The lid may include Ag/AgCl reference electrode, which the inventors have recognized as an importance reference electrode material in electrochemical applications. In the example illustrated in FIG. 10A, 24/96/384 reference electrodes and their control circuits are integrated on a PCB Lid with the same form factor as the standard well-plate. The control circuits may be programed with SPI so that customized experiments can be perform from well to well. The reference electrodes can measure solution/media voltage/current and apply stimulation to the experiment well. The lid design can additionally be used to accommodate a photodiode or a photoemitter lid for optical applications (e.g. optogenetic/optical electrochemical sensing).

Applications

FIGS. 11A, 11B and 11C illustrate several exemplary applications of the apparatus as disclosed herein. In addition to electrophysiology studies, a CMOS-Multiwell platform as described herein can also leverage impedance and electrochemical measurement to extend the area of applications.

For example, a CMOS-Multiwell platform may be used for cell or tissue mapping, such as spatial characterization of one or more characteristics of cells or tissues disposed on a surface of a well. Such characteristics may be related to one or more phenomena such as cell confluency, cell migration, cell viability/toxicity, and cell adhesion. In one non-limiting example, an impedance map between electrodes in the electrode array may be created that is representative of spatial distribution of cells relative to the electrodes.

As another exemplary use scenario, the CMOS-Multiwell platform as described herein may be used for performing patterned redox electrochemistry in selected spatial areas by selectively activating a select pattern of electrodes within a well. The patterned electrochemistry may be used to interact with a pattern of cells electrochemically, or to perform electrochemical sensing such as sensing of pH, $O_2$ level, etc. in selectively patterned spatial areas.

As a further example, the CMOS-Multiwell platform may be used for single-cell measurements, including but not limited to single-cell action potential or ion-channel measurements. The single-cell measurements may also include network measurements to characterize conduction velocity for cardiac cells, or synapse mapping of neurons in some non-limiting examples.

The following applications are each incorporated herein by references in their entireties: U.S. Provisional Patent Application Ser. No. 63/040,439, filed Jun. 17, 2020, by Park, et al.; U.S. Provisional Patent Application Ser. No. 63/040,424, filed Jun. 17, 2020, by Ham, et al.; and U.S. Provisional Patent Application Ser. No. 63/040,412, filed Jun. 17, 2020, by Ham, et al. In addition, the following are each incorporated herein by references in their entireties: a PCT patent application, filed on Jun. 16, 2021, entitled "Systems and Methods for Patterning and Spatial Electrochemical Mapping of Cells," and a PCT patent application, filed on Jun. 16, 2021, entitled "Apparatuses for Cell Mapping Via Impedance Measurements and Methods to Operate the Same."

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Further, though advantages of the present invention are indicated, it should be appreciated that not every embodiment of the technology described herein will include every described advantage. Some embodiments may not implement any features described as advantageous herein and in some instances one or more of the described features may be implemented to achieve further embodiments. Accordingly, the foregoing description and drawings are by way of example only.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

What is claimed is:

1. An apparatus for electrical assessment of a biological specimen, comprising:
    a plate having a multiple-well array for disposing thereon the biological specimen, each well of the multiple-well array having a plurality of electrodes disposed therein;
    a first substrate having a first surface facing wells of the multiple-well array of the plate and having a second surface opposite the first surface; and
    a multiwell integrated circuit disposed on or in the first substrate, the multiwell integrated circuit comprising:
        an array of reticle areas, each reticle area comprising complementary metal oxide semiconductor (CMOS) circuitry of a same design, wherein each reticle area comprises:
            at least one well circuit comprising a plurality of peripheral circuits in electrical communication with the plurality of electrodes in a well of the multiple-well array using a plurality of addressable switches coupled to each electrode;
            a reference voltage bias terminal; and
            an addressable switch located proximate to each electrode, the addressable switch configured to connect the reference voltage bias terminal to any set of the plurality of electrodes;
        wherein the multiple-well array comprises at least 24 wells; and
        wherein the multiple-well array includes at least 24 reticle areas to accommodate a standard number of wells in the multiple-well array.

2. The apparatus of claim 1, further comprising a lid coupled to a second side of the plate opposite a first side of the plate.

3. The apparatus of claim 2, wherein the lid comprises a plurality of photodetectors, each photodetector facing a corresponding well of the multiple-well array.

4. The apparatus of claim 1, further comprising a second substrate, wherein the second substrate has a plurality of conductive structures disposed at a first surface of the second substrate facing a mounting surface of the first substrate, and wherein each conductive structure is electrically connected to a corresponding pad of a plurality of pads on the mounting surface of the first substrate.

5. The apparatus of claim 4, wherein at least one of the second substrate and the first substrate comprises a magnetic element configured to generate a magnetic field to couple the first and second substrates via a magnetic force.

6. The apparatus of claim 1, further comprising an enclosure that surrounds the multiwell integrated circuit and the plate on at least five sides.

7. The apparatus of claim 1, wherein the plurality of electrodes each extend into a corresponding well of the multiple-well array so that when a cell is positioned within the well, one or more of the electrodes contact the cell.

8. The apparatus of claim 1, wherein in a reticle area of the array of reticle areas:
    the multiwell integrated circuit comprises a first plurality of conductors oriented along a first routing direction in a plane of the multiwell integrated circuit and second plurality of conductors oriented along a second routing direction in the plane of the multiwell integrated circuit different from the first routing direction;
    the first and second routing directions are orthogonal;
    the first plurality of conductors are configured to direct a signal of a first type along the first routing direction, and the second plurality of conductors are configured to direct a signal of a second type along the second routing direction; and
    the signal of the first type is a digital signal and the signal of the second type is an analog signal.

9. The apparatus of claim 8, wherein the reticle area is a first reticle area, the multiwell integrated circuit further comprising:
    a second reticle area comprising a routing circuit connected to the first plurality of conductors and configured to receive the signal of the first type from the first reticle area along the first routing direction; and
    a third reticle area comprising a routing circuit connected to the second plurality of conductors and configured to receive the signal of the second type from the first reticle area along the second routing direction.

10. The apparatus of claim 1, wherein each peripheral circuit comprises:
    a stimulation circuit selectively connectable to a subset of the plurality of electrodes through the plurality of addressable switches; and
    a recording circuit selectively connectable to the subset of the plurality of electrodes through the plurality of addressable switches,
    wherein the stimulation circuit comprises one or more current injectors; and
    wherein the recording circuit comprises a terminal configured to receive an electrical signal from the subset of the plurality of electrodes.

11. The apparatus of claim 1, wherein each well has an opening that is open towards the multiwell integrated circuit, wherein the plurality of electrodes comprise an array of conductors disposed on the first surface of the first substrate, and wherein the first surface of the first substrate is an electrically insulating surface.

12. The apparatus of claim 1, wherein the multiple-well array has a well-to-well distance between 4.5 mm and 9 mm.

13. The apparatus of claim 1, wherein reticle areas of the array of reticle areas are centered at a pitch of 18 mm or 9 mm.

14. The apparatus of claim 1, wherein the first substrate is a printed circuit board (PCB).

15. The apparatus of claim 1, comprising a plurality of conductors extending between at least two reticle areas of the array of reticle areas, wherein the at least one well circuit of each of the at least two reticle areas is connected to one or more conductors of the plurality of conductors so that the at least two reticle areas of
the array of reticle areas are in electrical communication with each other.

16. The apparatus of claim 15, wherein at least a portion of at least some of the plurality of conductors are disposed in a redistribution layer formed on the first surface of the first substrate.

17. The apparatus of claim 9, wherein the routing circuit of at least one of the first and second reticle areas comprises one or more shift registers configured to route the signal of the first type.

18. The apparatus of claim 1, wherein the plurality of electrodes comprises at least 1000 electrodes.

19. The apparatus of claim 18, wherein the plurality of electrodes comprises at least 4000 electrodes.

20. The apparatus of claim 1, wherein the at least one well circuit comprises a stimulation circuit comprising a current injector, wherein the stimulation circuit is selectively connectable to the plurality of electrodes through the plurality of addressable switches.

21. The apparatus of claim 1, further comprising one or more switches configured to selectively couple a subset of the plurality of peripheral circuits within the well circuit to one or more optoelectronic components.

22. The apparatus of claim 21, wherein the one or more optoelectronic components comprise a light-emitting diode, a photodetector, or a combination thereof.

23. The apparatus of claim 1, wherein:
the array of reticle areas is arranged in rows extending along a first direction parallel to a plane of the first substrate, and in columns along a second direction parallel to the plane of the first substrate;
adjacent reticle areas in each row are connected by an array of cross-reticle connections arranged along the second direction; and
adjacent reticle areas in each column are connected by an array of cross-reticle connections arranged along the first direction.

24. The apparatus of claim 9, wherein the routing circuit of at least one of the first and second reticle areas comprises at least one digital bus and at least one analog bus.

* * * * *